United States Patent [19]

Ibrahim et al.

[11] Patent Number: 5,716,988
[45] Date of Patent: Feb. 10, 1998

[54] PHARMACEUTICALLY STABLE PREPARATION OF OXALIPLATINUM

[75] Inventors: Houssam Ibrahim, Veyrier; Rolland-Yves Mauvernay, Lausanne, both of Switzerland

[73] Assignee: Debiopharm S.A., Lausanne, Switzerland

[21] Appl. No.: 776,240

[22] PCT Filed: Aug. 7, 1995

[86] PCT No.: PCT/IB95/00614

§ 371 Date: Jan. 24, 1997

§ 102(e) Date: Jan. 24, 1997

[87] PCT Pub. No.: WO96/04904

PCT Pub. Date: Feb. 22, 1996

[30] Foreign Application Priority Data

Aug. 8, 1994 [CH] Switzerland .............................. 2462/94

[51] Int. Cl.⁶ ............................................... A61K 31/28

[52] U.S. Cl. ............................................................ 514/492
[58] Field of Search ............................................. 514/492

[56] References Cited

U.S. PATENT DOCUMENTS 4,169,846  10/1979  Kidani et al. .................... 260/429 R

FOREIGN PATENT DOCUMENTS 0 486 998   5/1992   European Pat. Off. .
94/12193    6/1994   WIPO .

*Primary Examiner*—Raymond Henley, III
*Attorney, Agent, or Firm*—Young & Thompson

[57] ABSTRACT

A pharmaceutically stable oxaliplatinum preparation for parenteral administration comprises an aqueous solution of oxaliplatinum, in a concentration of 1 to 5 mg/ml, and with a pH in the range of 4.5 to 6. The aqueous oxaliplatinum solution is advantageously provided as a ready-to-use preparation in a sealed container.

9 Claims, No Drawings

PHARMACEUTICALLY STABLE PREPARATION OF OXALIPLATINUM

This is a 371 of PCT/IB95/00614 filed Aug. 7, 1995.

The present invention is concerned with a pharmaceutically stable preparation of oxaliplatinum for administration by the parenteral route.

Oxaliplatinum (International Nonproprietary Name) is an optical isomer prepared in 1978 by Y. Kidani from a mixture of diaminocyclohexane derivatives (dach-platinum), namely the cis-oxalato complex of platinum II, from the trans-1-1,2-diaminocyclohexane or according to "Who Drug Information" vol. 1, N° 4, 1987, the (oxalato (2-)0,0') platinum from the (1R,2R)-1,2-cyclohexane-diamine-N,N'. This complex compound of platinum is known to exhibit a therapeutic activity comparable or superior to that of other known complex compounds of platinum, such as cis-platinum for example.

As the latter, oxaliplatinum is a cytostatic antineoplastic agent which can be used in the therapeutic treatment of various types of cancers and, more particularly, those of the colon, of the ovaries, of the upper respiratory tract and also epidermoid cancers and cancers of germinal cells (testicles, mediastina, pineal gland, etc.). In addition to the above-mentioned examples of the use of oxaliplatinum, one can furthermore mention colon cancers which are resistant to pyrimidines, non-small cell lung cancers, non-Hodgkin's lymphoma, breast cancers, cancers of the upper respiratory/digestive tract, malignant melanoma, hepatocarcinoma, urothelial cancers, prostate cancers, etc, and more broadly, other types of solid tumors.

At the present time, oxaliplatinum is available for pre-clinical and clinical trials in vials as a lyophilisate, for reconstitution, just before the administration, with injectable water or an isotonic 5% glucose solution, and dilution with a 5% glucose solution, the administration being carried out by infusion, intravenously.

However, such a dosage form implies the use of a manufacturing process (lyophilization) which is relatively complicated and expensive as well as a reconstitution step at the time of use which requires both skill and care. Furthermore, in practice, such a method has proved to carry the risk of an error being made when reconstituting extemporaneously the solution; in actual fact, it is quite common for the reconstitution from lyophilisates of injectable pharmaceutical preparations or for diluting liquid preparations, to use a 0.9% NaCl solution; the mistaken use of such a solution in the case of the lyophilized form of oxaliplatinum would be quite harmful to the active principle, which would form a precipitate (dichloro-dach-platinum derivative) with NaCl and would bring about the rapid breakdown of said product.

Thus, in order to avoid all risk of misuse of the product and to make available to the medical practitioner or the nurse an oxaliplatinum preparation which may be used without requiring the above-mentioned operations, investigations were made to obtain an injectable solution of oxaliplatinum which would be ready to use and which, furthermore, would remain pharmaceutically stable before use for an acceptable duration of time according to recognized standards, and be easier and less expensive to manufacture than lyophilisates, while exhibiting a chemical purity (absence of isomerization) and a therapeutic activity equivalent to that of the reconstituted lyophilisate. This is the objective of the present invention.

The present inventors were able to show that this objective can be attained, in a totally surprising and unexpected manner, by using as the dose form for the administration by the parenteral route, an aqueous solution of oxaliplatinum, wherein the concentration of the active principle and the pH are within well determined respective ranges and wherein the active principle is free of any acidic or alkaline agent, buffer or other additive. It has been found, in particular, that aqueous solutions of oxaliplatinum having a concentration lesser than approximately 1 mg/ml are not sufficiently stable.

Accordingly, the object of the present invention is a stable pharmaceutical preparation of oxaliplatinum for administration by the parenteral route, wherein the oxaliplatinum is disolved in water at a concentration in the range from 1 to 5 mg/ml and at a pH in the range from 4.5 to 6, the oxaliplatinum content in the preparation representing at least 95% of the initial content and the solution remaining clear, colorless and free of any precipitate after a storage of a pharmaceutically acceptable duration. This preparation is free of any other components and should, in principle, not contain more than about 2% of impurities.

Preferably, the concentration in water of oxaliplatinum is about 2 mg/ml and the pH of the solution has an average value of about 5.3.

The stability of the aqueous solution of oxaliplatinum has also been confirmed by the measurement of the specific rotatory power, which ranges from +74.5° to +78.0°.

Thus, the term "pharmaceutically stable" should also be understood as referring to the stability of the specific rotatory power of oxaliplatinum, namely the optical purity of the solution (no isomerization). Further, the "pharmaceutically acceptable duration" during which the preparation according to the invention must remain stable should be understood here as corresponding to durations generally required in the art, i.e. for example during 3 to 5 years at room temperature or at the temperature of a refrigerator.

The manufacture of the preparation according to the invention can be carried out preferably by dissolving the oxaliplatinum in water suitable for injectable preparations, with a controlled stirring if required and preheating to about 40°, followed by a filtration for making the solution clear and one or more filtrations for making the solution sterile. After filling and closing of the primary containers selected, the preparation can further be sterilized by heating in an autoclave.

Preferably, the preparation according to the invention is in the form of an aqueous solution of oxaliplatinum which is ready for use and contained in a container, which is closed hermetically.

In a particular embodiment of the invention, the preparation according to the invention is provided as a unit active dose designed for administration by infusion and containing 50 or 100 mg of oxaliplatinum in an amount of water for injectable preparations selected according to the desired concentration.

This dose is advantageously contained in a vial made of neutral glass for pharmaceutical uses, closed by a stopper of which at least the surface extending inside the vial is inert with respect to the aqueous solution of oxaliplatinum, the space between said solution and said stopper being filled, if desired, by an inert gas.

The hermetically closed vial can also be, for example, a flexible pouch for infusion, an ampoule or furthermore a constituent member of an infusion device carrying an injection micropump.

The aqueous solution of oxaliplatinum can be administered intravenously by conventional means, when desired concomitantly with other agents, therapeutically active or not, under physicochemical conditions compatible with this platinum derivative and in accordance with practices accepted in cancer therapy.

Oxaliplatinum can be prescribed at doses ranging from 50 to 200 mg/m² of body surface, preferably from 100 to 130 mg/m² at each administration, the duration of the administration being of about 2 to 5 hours, the administrations being generally spaced apart by 3 to 5 weeks and the complete treatment comprising up to 6 to 10 administrations.

The invention will now be described in more detail with reference to the following examples concerning the injectable preparation according to the invention, its manufacture and its stability in the course of time

EXAMPLE 1

Preparation of the Aqueous Solution of Oxaliplatinum

In a thermostated container made of glass or stainless steel, there is introduced about 80% of the amount of the injectable water needed, and this water is warmed to 40° C.±5° while stirring (800–1200 rpm).

The amount of oxaliplatinum necessary for obtaining a concentration of, for example, 2 mg/ml, is weighed separately and added to the warmed water. The weighing container is rinsed thrice with injectable water, which is also added to the main mixture. The latter is further stirred at the temperature indicated during 30±5 minutes or longer if needed, until complete dissolution of oxaliplatinum. According to one version, nitrogen can be bubbled through the water to decrease its oxygen content.

The solution is then adjusted to its desired volume or weight by the addition of injectable water, and then homogenized during further 10±2 minutes (800–1200 rpm) and finally cooled to about 30° C., while still stirring. At this stage, samples of the solution are taken for carrying out the usual tests and controls and the solution is subjected to an aseptic filtration which produces a clear filtrate, in a manner known per se, and the solution is stored at 15°–30° C. before filling.

Preferably, one will use as the starting oxaliplatinum an apyrogenic product, of a pharmaceutical quality and optically pure (>99.9%), for example such as that obtained by the process patented by Tanaka K. K.

EXAMPLE 2

Packaging

The aqueous solution of oxaliplatinum, for example at a 2 mg/ml concentration, is then filled aseptically, preferably under an inert atmosphere, for example of nitrogen, into sterilized apyrogenic 50 ml glass vials.

To obtain a better stability of the aqueous solution of oxaliplatinum, one will use preferably a neutral glass of type I.

As to the stopper, one can use, for example, stoppers made of Teflon or of an elastomer based on halogenated butyls, possibly carrying an appropriate coating, in particular of a fluorinated polymer (for example of the "Omniflex" type, from Helvoet Pharma), so that at least the surface extending inside the vial be inert, with respect to the aqueous solution of oxaliplatinum.

The space between the stopper and the aqueous solution can be filled, if desired, with an inert gas, for example with nitrogen.

EXAMPLE 3

Stability Tests

Stability tests were carried out in the course of time on the aqueous solutions of oxaliplatinum obtained as described previously and stored in different containers, more particularly using two different stoppers, namely:

| Stopper A: | "Omniflex" |
|---|---|
| Stopper A(N): | "Omniflex" (with a head space filled with $N_2$) |
| Stopper B: | "Grey Butyl" (with a head space filled with $N_2$) |

The tests were carried out over 13 weeks and at several different temperatures, namely 5° C.±3° (temperature of a refrigerator), 27.5°±2.5° (ambient temperature), 40° (at 75% relative humidity) and 50° C. to produce an artificial acceleration of the phenomenon of degradation in the course of time; furthermore, the test at 27.5° was repeated in the presence of a strong light source (1100 lux).

The analytical method used is one currently practised in the art, namely high performance liquid chromatography (HPLC), for example as described in the Journal of Parenteral Drug Assoc., p. 108–109, 1979. The analysis of the peaks of the chromatogram, makes it possible to determine the content and the percentage of impurities, of which the main one was identified as being oxalic acid. Furthermore, for each test, the pH, the color and the opalescence of the solution were measured by conventional methods described in the pharmacopoeia.

The results obtained, which are summarized in the following table, demonstrate that under all the experimental conditions used, the stability of the aqueous solution of oxaliplatinum according to the invention can be considered as pharmaceutically acceptable, when considering the percentages of oxaliplatimum and those of impurities recovered, which were lower than required, even after more than 3 months of storage at 50° C. Also, the pH remained stable. Furthermore, all the solutions remained clear, colorless and free of solid particles visible with the naked eye. Finally, it was also demonstrated that the solutions remained optically pure (no isomerization), the measured rotatory power of oxaliplatinum being in the range form about +75.7° to about +76.2°, i.e. well between the limits required (+74.5° to +78.0°).

Another series of measurements at ambient temperature and at 40° C. also confirmed the stability of the aqueous solution of oxaliplatinum over a period in excess of 10 months.

TABLE

| Test ref. (stopper) | Storage conditions (°C.) | Oxaliplatimum recovered (% of initial) | Impurities (%) | pH |
|---|---|---|---|---|
| A | 5 ± 3 | 101.0 | 0.18 | 5.35 |
| A(K) | " | 101.0 | 0.28 | 5.35 |
| B | " | 100.0 | 0.28 | 5.34 |
| A | 27.5 ± 2.5 | 100.0 | 0.29 | 5.37 |
| A(N) | " | 100.0 | 0.31 | 5.33 |
| B | " | 100.5 | 0.31 | 5.36 |
| A | 27.5/1100 lux | 100.5 | 0.34 | 5.34 |
| A(N) | " | 99.5 | 0.42 | 5.29 |
| B | " | 100.0 | 0.40 | 5.37 |
| A | 40 (75% RH) | 100.0 | 0.35 | 5.45 |
| A(N) | " | 100.5 | 0.35 | 5.50 |
| B | " | 99.5 | 0.63 | 5.47 |
| A | 50 | 99.5 | 0.49 | 5.57 |
| A(N) | " | 99.0 | 0.54 | 5.65 |
| B | " | 99.0 | 1.16 | 5.59 |

We claim:

1. A pharmaceutically stable preparation of oxaliplatinum for the administration by the parenteral route, consisting of a solution of oxaliplatinum in water at a concentration of 1 to 5 mg/ml and having a pH of 4.5 to 6, the oxaliplatinum content in the preparation being at least 95% of the initial content and the solution remaining clear, colorless and free of precipitate after storage for a pharmaceutically acceptable duration of time.

2. A preparation according to claim 1, in which the concentration of oxaliplatinum is of about 2 mg/ml of water and the pH of the solution has an average value of about 5.3.

3. A preparation according to claim 1, in which the solution of oxaliplatinum has a specific rotatory power in the range from +74.5° to +78.0°.

4. A preparation according to claim 1, in the form of an aqueous solution of oxaliplatinum ready to be used and contained in a hermetically sealed container.

5. A preparation according to claim 4, characterized in that said container contains an active unit dose of 50 to 100 mg of oxaliplatinum, which can be administered by infusion.

6. A preparation according to claim 4, characterized in that said container is a glass vial for pharmaceutical use and is closed with a stopper of which, at least, the surface extending inside the vial is inert with respect to said solution.

7. A preparation according to claim 4, characterized in that said container is a flexible pouch for infusion or an ampoule.

8. A packaged pharmaceutical product comprising a glass vial closed with a stopper, said vial containing a pharmaceutically stable preparation of oxaliplatinum consisting of a solution of oxaliplatinum in water at a concentration of 1 to 5 mg/ml and having a pH of 4.5 to 6, the oxaliplatinum content in the preparation being at least 95% of the initial content and the solution remaining clear, colorless and free of precipitate after storage for a pharmaceutically acceptable duration; wherein said stopper has an inner surface which is inert with respect to said solution, said vial further comprising inert gas filling a space between said solution and said stopper.

9. A pharmaceutical product comprising an infusion device having an injection micropump, and a container containing a pharmaceutically stable preparation of oxaliplatinum consisting of a solution of oxaliplatinum in water at a concentration of 1 to 5 mg/ml and having a pH of 4.5 to 6, the oxaliplatinum content in the preparation being at least 95% of the initial content and the solution remaining clear, colorless and free of precipitate after storage for a pharmaceutically acceptable duration.

* * * * *